United States Patent
Mandrusov et al.

(10) Patent No.: US 7,460,914 B2
(45) Date of Patent: *Dec. 2, 2008

(54) DEVICES AND METHODS TO STIMULATE THERAPEUTIC ANGIOGENESIS FOR ISCHEMIA AND HEART FAILURE

(75) Inventors: Evgenia Mandrusov, Santa Clara, CA (US); Paul Consigny, San Jose, CA (US); Rodney W. Salo, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 307 days.

This patent is subject to a terminal disclaimer.

(21) Appl. No.: 11/244,016

(22) Filed: Oct. 5, 2005

(65) Prior Publication Data

US 2006/0030810 A1    Feb. 9, 2006

Related U.S. Application Data

(62) Division of application No. 10/246,249, filed on Sep. 18, 2002, now Pat. No. 7,400,931.

(51) Int. Cl.
*A61N 1/05* (2006.01)
*A61N 1/372* (2006.01)
*A61M 25/00* (2006.01)

(52) U.S. Cl. .................. 607/120; 607/3; 604/20; 604/19

(58) Field of Classification Search .................. 607/1–5, 607/9, 50, 120–123; 604/500–510, 96.01, 604/103.01, 19–21, 919, 27–28, 41, 43, 59–67, 604/82–85, 93.01, 95.05, 102.02, 102.03, 604/103.02, 103.03, 522, 890.1, 891.1, 892.1; 606/41

See application file for complete search history.

(56) References Cited

U.S. PATENT DOCUMENTS 5,083,564 A    1/1992    Scherlag (Continued)

FOREIGN PATENT DOCUMENTS

WO    WO-9815317 A1    4/1998

(Continued)

OTHER PUBLICATIONS

Al-Khadra, A., et al., "The Role of Electroporation in Defibrillation", *Circulation Research*, 87(9), Oct. 2000),797-804.

(Continued)

*Primary Examiner*—Kennedy J. Schaetzle
*Assistant Examiner*—Jessica Reidel
(74) *Attorney, Agent, or Firm*—Schwegman, Lundberg & Woessner, P.A.

(57) ABSTRACT

A method for stimulating angiogenesis is provided that includes the use of an electrical output channel adapted to deliver a sub-threshold voltage, a lead that includes a proximal end adapted to be electrically connected to the electrical output channel and a distal end adapted to be placed in the blood conduit where the distal end of the lead is adapted to deliver a treatment agent that stimulates therapeutic angiogenesis, and at least one electrode on the distal end of the first lead.

18 Claims, 14 Drawing Sheets

U.S. PATENT DOCUMENTS

| | | | |
|---|---|---|---|
| 5,320,642 | A | 6/1994 | Scherlag |
| 5,381,790 | A | 1/1995 | Kanesaka |
| 5,433,735 | A | 7/1995 | Zanakis et al. |
| 5,634,899 | A | 6/1997 | Shapland et al. |
| 5,755,766 | A | 5/1998 | Chastain et al. |
| 5,807,306 | A | 9/1998 | Shapland et al. |
| 5,876,399 | A | 3/1999 | Chia et al. |
| 5,941,868 | A * | 8/1999 | Kaplan et al. ............... 604/500 |
| 5,944,710 | A | 8/1999 | Dev et al. |
| 6,007,476 | A | 12/1999 | Wascher et al. |
| 6,024,739 | A | 2/2000 | Ponzi et al. |
| 6,059,726 | A | 5/2000 | Lee et al. |
| 6,086,582 | A | 7/2000 | Altman et al. |
| 6,123,084 | A | 9/2000 | Jandak et al. |
| 6,141,594 | A | 10/2000 | Flynn et al. |
| 6,165,164 | A | 12/2000 | Hill et al. |
| 6,236,887 | B1 | 5/2001 | Ben-Haim et al. |
| 6,254,573 | B1 | 7/2001 | Haim et al. |
| 6,298,272 | B1 | 10/2001 | Peterfeso et al. |
| 6,309,370 | B1 | 10/2001 | Haim et al. |
| 6,345,204 | B1 | 2/2002 | Scheiner et al. |
| 6,358,247 | B1 | 3/2002 | Altman et al. |
| 6,363,286 | B1 | 3/2002 | Zhu et al. |
| 6,416,510 | B1 | 7/2002 | Altman et al. |
| 6,463,334 | B1 | 10/2002 | Flynn et al. |
| 6,468,263 | B1 * | 10/2002 | Fischell et al. ............ 604/890.1 |
| 6,540,725 | B1 | 4/2003 | Ponzi |
| 6,544,270 | B1 | 4/2003 | Zhang |
| 6,547,787 | B1 | 4/2003 | Altman et al. |
| 6,560,489 | B2 | 5/2003 | Hauck |
| 6,575,931 | B1 | 6/2003 | Ponzi |
| 6,623,473 | B1 | 9/2003 | Ponzi |
| 6,623,474 | B1 | 9/2003 | Ponzi |
| 6,702,744 | B2 * | 3/2004 | Mandrusov et al. ......... 600/439 |
| 6,702,777 | B2 | 3/2004 | Haim et al. |
| 6,810,286 | B2 | 10/2004 | Donovan et al. |
| 6,855,124 | B1 | 2/2005 | Gonzalez et al. |
| 6,905,476 | B2 | 6/2005 | Ponzi |
| 6,909,920 | B2 | 6/2005 | Lokhoff et al. |
| 6,931,286 | B2 | 8/2005 | Sigg et al. |
| 2001/0031986 | A1 | 10/2001 | Hauck |
| 2001/0044619 | A1 | 11/2001 | Altman |
| 2002/0010492 | A1 | 1/2002 | Donovan et al. |
| 2002/0016615 | A1 | 2/2002 | Dev et al. |
| 2002/0022863 | A1 | 2/2002 | Hauck |
| 2002/0026228 | A1 | 2/2002 | Schauerte |
| 2002/0058981 | A1 | 5/2002 | Zhu et al. |
| 2002/0183720 | A1 | 12/2002 | Hill et al. |
| 2003/0032938 | A1 * | 2/2003 | Altman ...................... 604/509 |
| 2003/0113303 | A1 | 6/2003 | Schwartz |
| 2003/0125615 | A1 | 7/2003 | Schwartz |
| 2003/0129750 | A1 | 7/2003 | Schwartz |
| 2003/0171723 | A1 | 9/2003 | Ponzi |
| 2003/0195470 | A1 | 10/2003 | Ponzi |
| 2004/0122484 | A1 | 6/2004 | Hatlestad et al. |
| 2004/0186546 | A1 | 9/2004 | Mandrusov et al. |
| 2004/0213770 | A1 | 10/2004 | Seward et al. |
| 2004/0214182 | A1 | 10/2004 | Sharma et al. |
| 2004/0215251 | A1 | 10/2004 | Sharma et al. |
| 2005/0137671 | A1 | 6/2005 | Liu et al. |

FOREIGN PATENT DOCUMENTS

| | | | |
|---|---|---|---|
| WO | WO 00/74773 A1 * | 12/2000 | |

OTHER PUBLICATIONS

Avitall, B., et al., "Iontophoretic transmyocardial drug delivery. A novel approach to antiarrhythmic drug therapy.", *Circulation*, 85(4), (Apr. 1992), 1582-93.

Flynn, David M., et al., "Extendable and Retractable Lead Having a Snap-Fit Terminal Connector", U.S. Appl. No. 11/173,664, filed Jul. 1, 2005, 53 Pages.

Kanno, S., et al., "Establishment of a simple and practical procedure applicable to therapeutic angiogenesis", *Circulation*, 99(20), (May 25, 1999), 2682-2687.

Kaye, D. M., et al., "Frequency-dependent activation of a constitutive nitric oxide synthase and regulation of contractile function in adult rat ventricular myocytes", *Circulation Research*, 78(2), (Feb. 1996), 217-24.

Labhasetwar, V., et al., "Iontophoresis for Modulation of Cardiac Drug Delivery in Dogs", *Proceedings of the National Academy of Sciences USA*, 92(7), (Mar. 28, 1995), 2612-2616.

Mansourati, J., et al., "Left ventricular-based pacing in patients with chronic heart failure: comparison of acute hemodynamic benefits according to underlying heart disease", *Eur J Heart Fail.*, 2(2), (Jun. 2000), 195-9.

Qu, J, et al., "HCN2 overexpression in newborn and adult ventricular myocytes: distinct effects on gating and excitability", *Circ. Res.*, vol. 89(1), (Jul. 6, 2001), e8-14.

Qu, J, et al., "Sympathetic innervation alters activations of pacemaker current (If) in rat ventricle", *J. Physiol*, 526 Pt 3, (Aug. 1, 2000), 561-569.

Shi, W, et al., "Distribution and prevalence of hyperpolarization-activated cation channel (HCN) mRNA expression in cardiac tissues", *Circ. Res.*, vol. 85(1), (Jul. 9, 1999), e1-6.

Yu, H., et al., "MinK-related peptide 1: A beta subunit for the HCN ion channel subunit family enhances expression and speeds activation", *Circ. Res.*, 88(12), (Jun. 22, 2001), e84-7.

"U.S. Appl. No. 10/246,249, Response filed Sep. 12, 2007 to Non-Final Office Action mailed Jul. 12, 2007", 17 pgs.

"U.S. Appl. No. 10/246,249, Notice of Allowance mailed Dec. 19, 2007", 11 pgs.

* cited by examiner

DEVICES AND METHODS TO STIMULATE THERAPEUTIC ANGIOGENESIS FOR ISCHEMIA AND HEART FAILURE

CROSS-REFERENCE TO RELATED APPLICATIONS

This application is a division of U.S. patent application Ser. No. 10/246,249, filed on Sep. 18, 2002, now U.S. Pat. No. 7,400,931 the specification of which is incorporated herein by reference.

FIELD

Resolving ischemia by inducing formation of blood vessels through therapeutic angiogenesis.

RELEVANT ART

A major component of morbidity and mortality attributable to cardiovascular disease occurs as a consequence of the partial or complete blockage of vessels carrying blood in the coronary and/or peripheral vasculature. When such vessels are partially occluded, lack of blood flow causes ischemia to the muscle tissues supplied by such vessel, consequently inhibiting muscle contraction and proper function. Total occlusion of blood flow causes necrosis of the muscle tissue. Necrosis of muscle tissue causes scar formation, leading to cardiac remodeling and failure.

Blood vessel occlusions are commonly treated by mechanically enhancing blood flow in the affected vessels. Such mechanical enhancements are often provided by employing surgical techniques that attach natural or synthetic conduits proximal and distal to the areas of occlusion, thereby providing bypass grafts, or revascularization by various means to physically enlarge the vascular lumen at the site of occlusion. These revascularization procedures involve such devices as balloons, endovascular knives (atherectomy), and endovascular drills. The surgical approach is accompanied by significant morbidity and even mortality, while the angioplasty-type processes are complicated by recurrent stenoses in many cases.

In some individuals, blood vessel occlusion is partially compensated by natural processes, in which new vessels are formed (termed "angiogenesis") and small vessels are enlarged (termed "arteriogenesis") to replace the function of the impaired vessels. These new conduits may facilitate restoration of blood flow to the deprived tissue, thereby constituting "natural bypasses" around the occluded vessels. However, some individuals are unable to generate sufficient collateral vessels to adequately compensate for the diminished blood flow caused by cardiovascular disease. Accordingly, it would be desirable to provide a composition, kit and methods for delivering a composition to help stimulate the natural process of therapeutic angiogenesis to compensate for blood loss due to an occlusion in a coronary and peripheral arteries in order to treat ischemia.

U.S. Pat. No. 5,433,735 discloses regeneration of damaged tissue that begins with the growth and proliferation of cells which takes place along a migratory path and in a polar direction.

U.S. Pat. No. 5,944,710 discloses a method for sustained intravascular delivery via electroporation.

U.S. Pat. No. 6,007,476 discloses a method and apparatus for affecting angiogenesis in biological subjects such as mammals.

U.S. Pat. No. 6,024,739 discloses a method for direct myocardial revascularization by providing a catheter.

U.S. Pat. No. 6,123,084 discloses a method for improving blood flow in the heart that provides a catheter system.

U.S. patent application No. US 2001/0031986 A1, published on Oct. 18, 2001, discloses an apparatus and method for conferring a therapeutic current to the heart.

U.S. patent application No. US 2002/0010492 A1, published on Jan. 24, 2002, discloses a stimulatory device for the controlled production of angiogenic growth factors.

U.S. patent application No. US 2002/0022863 A1, published on Feb. 21, 2002, discloses an apparatus and method for conferring a therapeutic current on the heart.

U.S. patent application No. US 2002/0026228 A1, published on Feb. 28, 2002, discloses an electrode for intravascular stimulation, cardioversion and/or defibrillation.

SUMMARY

In one embodiment, there is disclosed a device that includes an electrical output channel adapted to deliver a sub-threshold voltage; a lead that includes a proximal end adapted to be electrically connected to the electrical output channel and a distal end adapted to be placed in a blood conduit, where the distal end of the lead is adapted to deliver a treatment agent that stimulates angiogenesis; and at least one electrode on the distal end of the first lead. Representatively, the device may be used to stimulate artenogenesis and/or angiogenesis by the delivery of electrical energy (e.g., pulses) to a treatment site. In addition, a lead such as described may deliver a treatment agent to a treatment site to work in concert with the electrical energy to stimulate arteriogenesis or angiogenesis. Alternatively, arteriogenesis or angiogenesis may be stimulated using a device that delivers a treatment agent by iontophoresis and/or electroporation.

In another embodiment, there is disclosed a method for stimulating angiogenesis that includes positioning an electrode on a lead at a location in a blood vessel; connecting the lead to an electrical output channel adapted to deliver a sub-threshold voltage; activating the electrical output channel to deliver the sub-threshold voltage through the lead to the electrode; and delivering a treatment agent adapted to stimulate angiogenesis at the location.

BRIEF DESCRIPTION OF THE DRAWINGS

The features of the described embodiments are specifically set forth in the appended claims. However, the embodiments are best understood by referring to the following description and accompanying drawings, in which similar parts are identified by like reference numerals.

DETAILED DESCRIPTION

Figure 1:
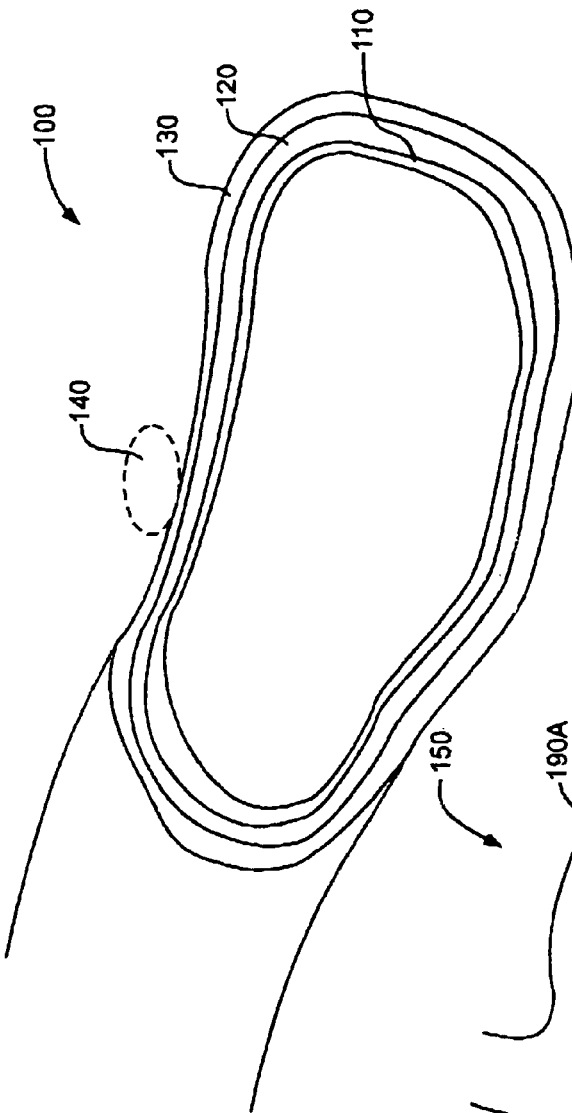
FIG. 1 schematically illustrates a perspective and cross-sectional view of a blood vessel.

In connection with the description of the various embodiments, the following definitions are utilized:

"Therapeutic angiogenesis" refers to the processes of causing or inducing angiogenesis and arteriogenesis.

"Angiogenesis" is the promotion or causation of the formation of new blood vessels in the ischemic region.

"Arteriogenesis" is the enlargement of pre-existing collateral vessels. The collateral vessels allow blood to flow from a well-perfused region of the vessel into the ischemic region.

"Ischemia" is a condition where oxygen demand of the tissue is not met due to localized reduction in blood flow caused by narrowing or occlusion of one or more vessels. Narrowing of arteries such as coronary arteries or their branches, is most often caused by thrombosis or via deposits of fat, connective tissue, calcification of the walls, or restenosis due to abnormal migration and proliferation of smooth muscle cells.

"Occlusion" is the total or partial obstruction of blood flow through a vessel.

"Treatment agent" includes agents directed to specific cellular binding sites (e.g., receptor binding treatment agents), drugs, medicaments and agents that induce inflammation.

"Specific binding treatment agent" or "receptor binding treatment agent" includes a protein, gene or small molecule that will induce and/or modulate a therapeutic angiogenic response through interaction with a specific binding site (e.g., a binding within a cell or on a cell surface). Representative treatment agents include, but are not limited to, vascular endothelial growth factor (VEGF) in any of its multiple isoforms, fibroblast growth factors, monocyte chemoattractant protein 1 (MCP-1), transforming growth factor beta (TGF-beta) in any of its multiple isoforms, transforming growth factor alpha (TGF-alpha), lipid factors, hypoxia-inducible factor 1-alpha (HIF-1-alpha), PR39, DEL 1, nicotine, insulin-like growth factors, placental growth factor (PlGF), hepatocyte growth factor (HGF), estrogen, follistatin, proliferin, prostaglandin E1, prostaglandin E2, cytokines, tumor necrosis factor (TNF-alpha), erythropoietin, granulocyte colony-stimulating factor (G-CSF), granulocyte macrophage colony-stimulating factor (GM-CSF), angiogenin, hormones, and genes that encode such substances.

"Non-specific treatment agent" includes various agents that induce inflammation. Examples include bioresorbable inorganic compounds such as sol gel particles and calcium phosphate glass including iron; fibrin, gelatin, low molecular weight hyaluronic acid, and chitin; bacterial polysaccharides; and metals.

"Carrier" includes a matrix that contains one or more treatment agents. A suitable carrier may take the form of a nanoparticle (e.g., nanosphere) or microparticle (e.g., microsphere) as the situation may dictate.

"Threshold voltage" is the voltage required to generate a specific biologic response.

"Electroporation" is a temporary condition where an outer membrane of a cell briefly becomes porous due to the application of an electric field.

"Iontophoresis" is a current-facilitated transport of charged entities.

"Lead" is an apparatus to be implanted within a patient having at least one of an electrical, liquid, or solid conduit.

"Electrode" is a portion of an electrical conduit to be implanted within a patient to conduct electricity from the conduit to the patient, or from the patient to the conduit.

Referring to FIG. 1, a non-diseased artery is illustrated. Artery 100 includes an arterial wall having a number of layers. Innermost layer 110 is generally referred to as the intimal layer that includes the endothelium, the subendothelial layer, and the internal elastic lamina. Media layer 120 is concentrically outward from intimal layer 110 and adventitial layer 130 is the outermost layer. Beyond adventitial layer 130 lies the extravascular tissue including, adjacent adventitial layer (and possibly including a portion of adventitial layer), periadvential site or area 140.

Figure 2:
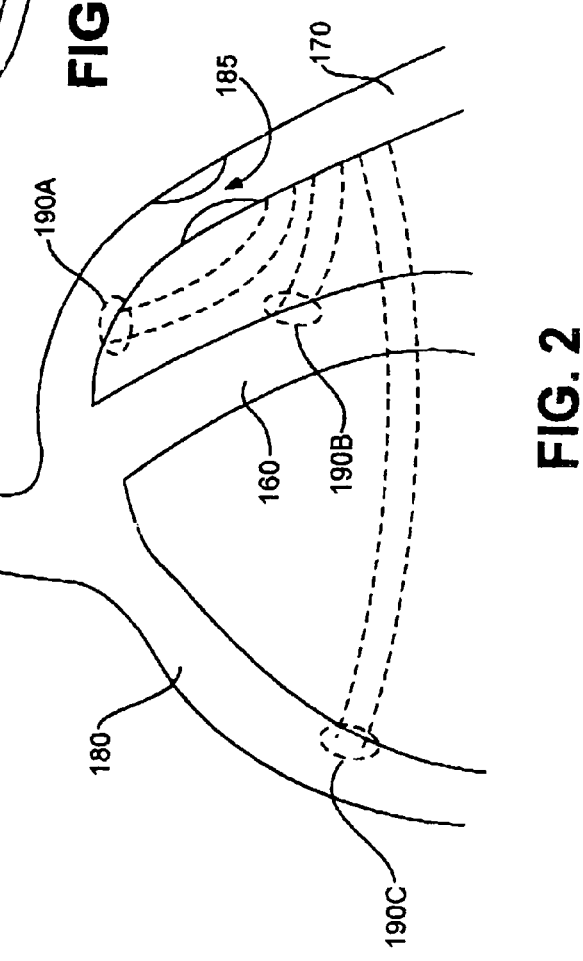
FIG. 2 schematically illustrates a planar cross-sectional view of components of a coronary artery network.
Figure 11:
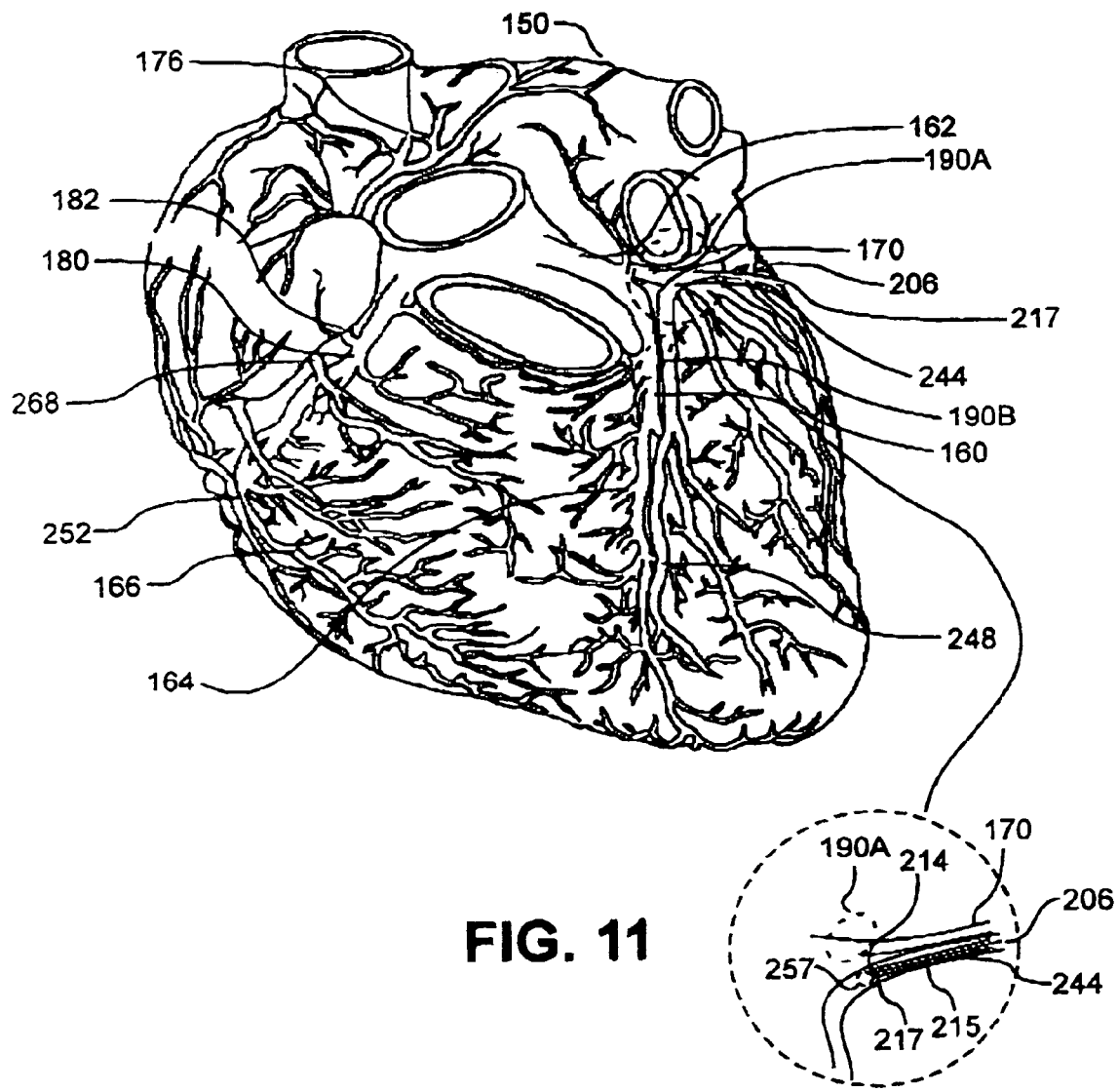
FIG. 11 schematically illustrates the coronary arteries and cardiac veins on the sternocostal surface on the exterior of the heart.
Figure 12:
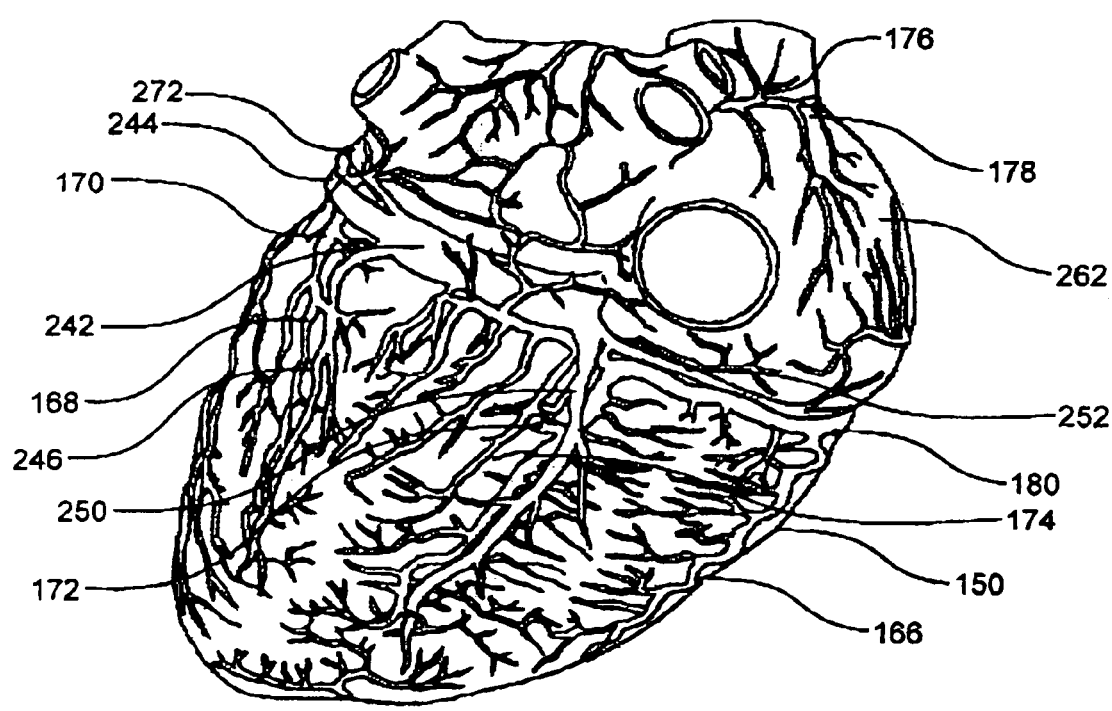
FIG. 12 schematically illustrates the coronary arteries and cardiac veins on the diaphragmatic surface on the exterior of the heart.

FIG. 2 illustrates a simplified view of a few of the components of the coronary artery network shown in FIGS. 11 and 12. In this simplified example, vasculature 150 includes left anterior descending artery (LAD) 160, left circumflex artery (LCX) 170 and right coronary artery (RCA) 180. Occlusion 185 is shown in LCX 170. Occlusion 185 limits the amount of oxygenated blood flow through LCX 170 resulting in ischemia in the tissue that is supplied by the LCX and distal to the occlusion.

To improve the function of the artery network, it is generally desired to either remove occlusion 185 (for example through an angioplasty procedure), bypass occlusion 185 or induce therapeutic angiogenesis to makeup for the constriction in the ischemic region (e.g., downstream of occlusion 185). FIG. 2 shows therapeutic angiogenesis induced at sites 190A (associated with LCX 170); 190B (associated with LAD 160); and 190C (associated with RCA 180). By inducing therapeutic angiogenesis at sites 190A, 190B, and 190C, permanent revascularization of the network is accomplished, thus compensating for reduced flow through LCX 170. The following paragraphs describe compositions, methods, and devices suitable for inducing therapeutic angiogenesis.

Figure 3:
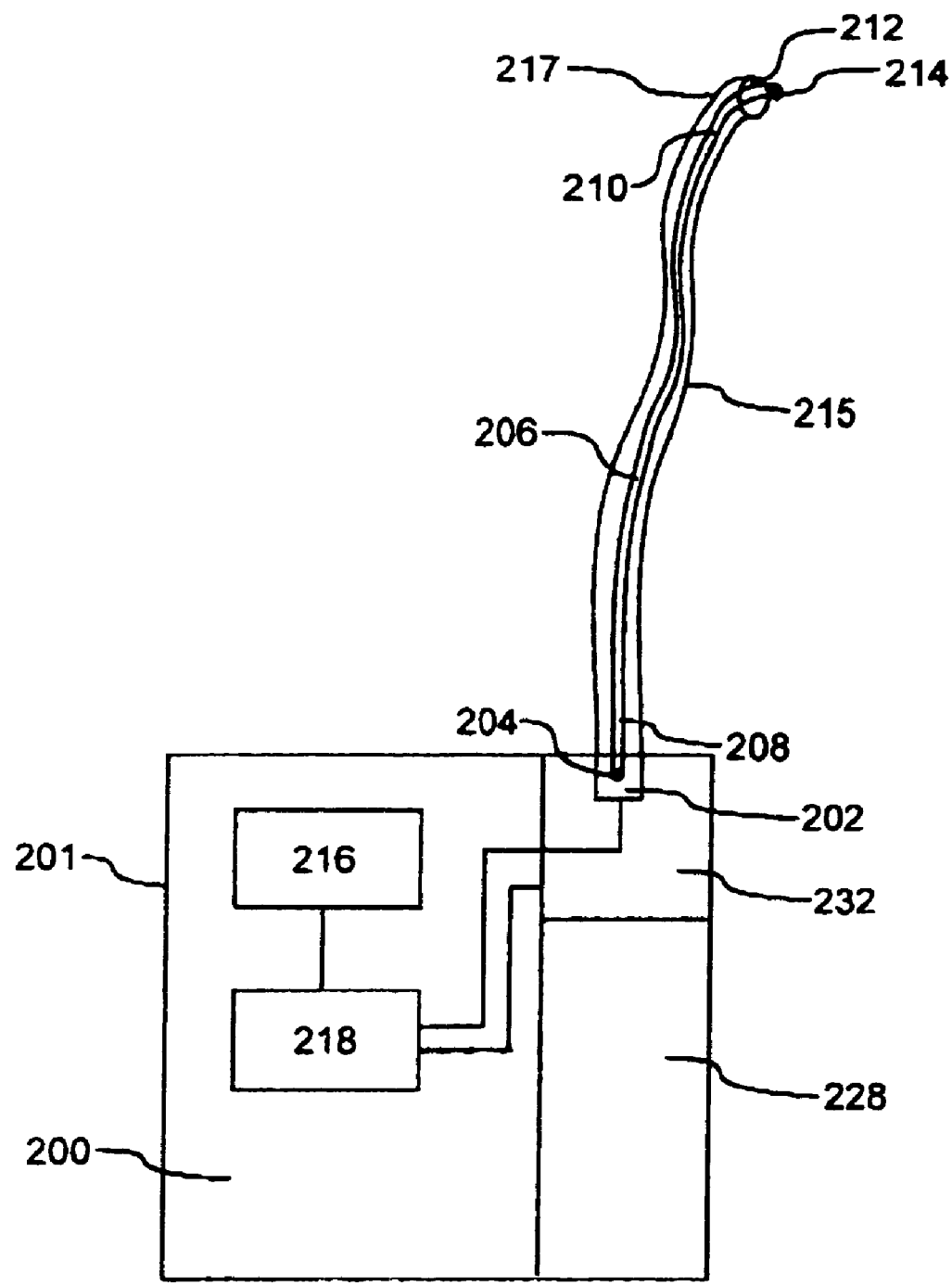
FIG. 3 schematically illustrates a device having one lead and an electrode on the distal end of the lead.

A first embodiment of a device that may be used for stimulating therapeutic angiogenesis is illustrated in FIG. 3. Device 200 may be similar in size to modem pacemakers and defibrillators. Representatively, device 200 includes housing 201 that contains power source 216, in one embodiment, a 12 volt lithium battery, and electronic circuitry 218 to generate electrical energy signals (e.g., pulses) and control the timing of the electrical energy and the amount of energy delivered. Electronic circuitry 218 includes, for example, a processor containing machine-readable program instructions (e.g., instruction logic) to control the timing and delivery of electrical energy. Device 200 includes first electrical output channel 202 (coupled to power source 216 and/or circuitry 218) connected to lead 206 by connection 204. In one embodiment, connection 204 is, for example, a (pinch) type connection. In order to energize lead 206, connection 204 between lead 206 and device 200 must be made, but device 200 can be packaged and sold without connection 204 having been made.

In one embodiment, lead 206 includes a conductive material, such as MP35N (a stainless steel alloy) with a silver core, on the order of about 0.005 inches in diameter, that is optionally insulated about its length. Lead 206 includes proximal end 208 adjacent to connection 204 and distal end 210. Distal end 210 includes electrode 214. Electrode 214 delivers electrical energy from first electrical output channel 202. In one embodiment, first electrical output channel 202 can deliver a sub-threshold voltage, or an above-threshold output voltage. In one context, a threshold voltage is defined as the voltage required to generate a specific biologic response, for example, ventricular contraction, atrial contraction, defibrillation, etc. In one embodiment, the sub-threshold voltage is less than about 1.5 volts. In another embodiment, the sub-threshold voltage is less than about 1.0 volts. In another embodiment, the sub-threshold voltage is less than about 0.75 volts. In another embodiment, the sub-threshold voltage is less than about 0.5 volts. In another embodiment, the sub-threshold voltage is less than about 0.1 volts.

In one embodiment, a threshold voltage is defined as the voltage required to generate a specific biologic response, in this embodiment, a pacing voltage. A pacing voltage is the voltage required as the output of a pacemaker to cause a local depolarization of cardiac myocyte cell membranes, initiating a wave of depolarization. In another embodiment, the threshold voltage is defined as the voltage required to generate a specific biologic response, in this embodiment, a defibrillation. Defibrillation is the voltage required to shock the heart back into a normal rhythm when the heart is in fibrillation. In contrast to a pacing voltage, a defibrillation voltage is generally much higher. A pacing voltage as a threshold voltage is generally a low voltage, while a defibrillation voltage as a threshold voltage is generally a high voltage.

As noted above, device 200 may be similar in size to modem pacemakers or defibrillators. In one embodiment, device 200 may be suitable for use as a pacemaker or defibrillator with electronic circuitry 218 configured to deliver the appropriate electrical energy (e.g., pulse) for pacemaker or defibrillator operation (e.g., through one or more other leads (not shown), as well as the electrical energy (e.g., pulse) through lead 206 to stimulate therapeutic angiogenesis). In the example of a pacemaker operation, electronic circuitry 218 generally delivers electrical energy according to a threshold voltage, to selected areas of the heart according to a predetermined rhythm. In addition to this rhythmic delivery, electronic circuitry 218 delivers electrical energy to an area selected for therapeutic angiogenesis. The delivery of electrical energy signals to lead 206 may occur, for example, between signals generated for a pulsing rhythm. A machine-readable program readable by a processor included with electronic circuitry may be used to coordinate the delivery of electronic signals.

Figure 4:
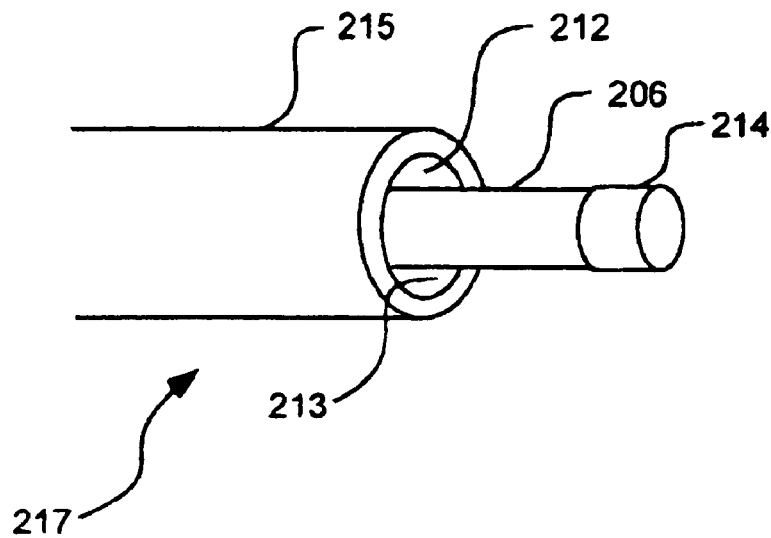
FIG. 4 schematically illustrates one embodiment of the distal end of a lead.

In one embodiment, connection 204 is used as an electrical connection and as a connection to deliver a treatment agent to distal end 210 of lead 206. There is provided pump 232 adjacent to the connection for delivering the treatment agent from reservoir 228. Pump 232 is operated (controlled) by electronic circuitry 218 to transfer a treatment agent from reservoir 228 to connection 204. A machine readable program included in electronic circuitry 218 may include program instructions for the delivery of a treatment agent (timing and amount/volume) from pump 232 through cannula 215. In one embodiment, cannula or sheath 215 is coupled to connection 204. Cannula 215 is made, in one embodiment, of a flexible material, for example a polymeric material, such as polymers of ethylene, propylene, butylene, or copolymers thereof, and has an external diameter suitable for advancing through a blood vessel of a human patient. Cannula 215 also includes distal end 217 with lumen 212 extending therethrough. In one embodiment, lead 206 is disposed within lumen 212 of cannula 215. FIG. 4 is a magnified perspective view of one embodiment of distal end 217 of cannula 215 showing lead 206 disposed within lumen 212. In this embodiment, the outer diameter of lead 206 is smaller than the inner diameter 212 of cannula 215, leaving an annular lumen or space 213 for storage or flow of a liquid and/or a solid treatment agent. Cannula 215 includes lumen 213 therethrough from proximal end 216 at connection 204 to distal end 217. As illustrated, the electrical connection from device 200 to distal end 210 of lead 206 to electrode 214 is made through lumen 212 of sheath 215 (e.g., coaxially aligned).

Figure 5:
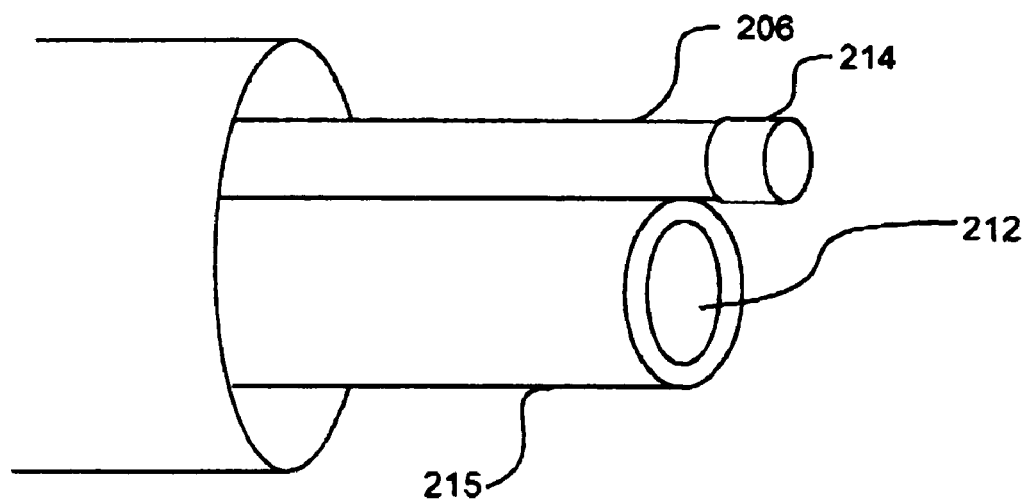
FIG. 5 schematically illustrates one embodiment of the distal end of a lead.

In another embodiment, as shown in FIG. 5, lead 206 may be disposed on the exterior of cannula 215 (e.g., colinearly aligned) and possibly connected thereto (e.g., via an adhesive) with optional sheath 216 surrounding a portion of lead 206 and cannula 215 and leaving a distal end of lead 206 (e.g., including a portion of electrode 214 exposed).

As described above, device 200 could include pump 232 (shown in FIG. 3) for delivering the treatment agent. Alternatively, other dispensing mechanisms may be employed. Such mechanisms include, but are not limited to, establishing a pressure differential between reservoir 228 and distal end 217 of lumen 212 (e.g., a gravity feed), a delayed release mechanism, a drip, and a solid treatment agent fed through or stored in lumen 212.

Reservoir 228 in housing 201 of device 200 is of a size suitable for storing a sufficient amount/volume of a treatment agent for delivery to a treatment site. In one embodiment, reservoir 228 has a storage volume of about 0.1-20 mL which allows storage of an amount of treatment that may be delivered over a period of a few days or a few weeks (e.g., about 5-20 µl/day).

Figure 6:
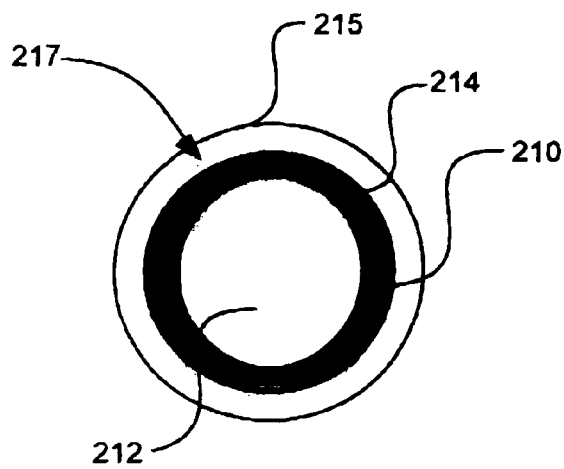
FIG. 6 schematically illustrates one embodiment of the distal end of a lead.
Figure 7:
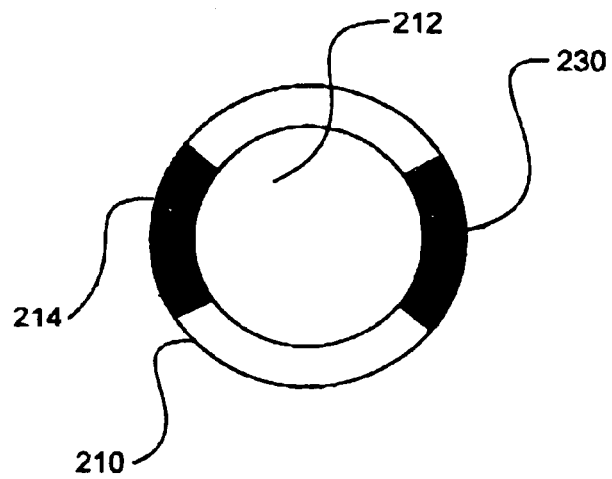
FIG. 7 schematically illustrates one embodiment of the distal end of a lead.
Figure 8:
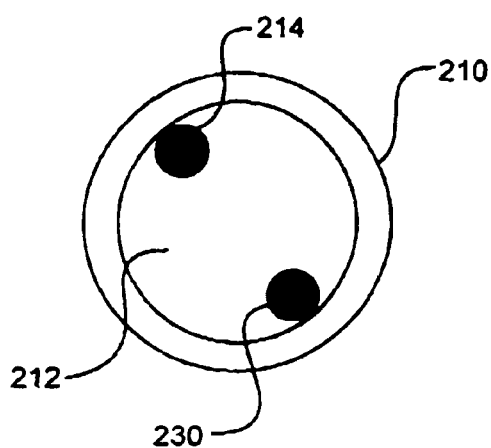
FIG. 8 schematically illustrates one embodiment of the distal end of a lead.

In addition to the above embodiment describing lead/lumen orientation, FIGS. 6-8 show alternative embodiments. Reference numbers similar to those used above with regard to FIGS. 3-5 are used to facilitate understanding of various other representative configurations or orientations of leads and lumens. Referring now to FIG. 6, another embodiment of distal end 210 of lead 206 and cannula 215 is illustrated. Cannula 215 has lumen 212 running therethrough that creates an annular space. Lumen 212 may be used for the storage and/or delivery of a liquid and/or solid treatment agent. Electrode 214 is shown at distal end 217 about lumen 212. As shown, electrode 214 is on the interior wall of cannula 215 adjacent lumen 212 (e.g., a tubular inner lead 206). Alternatively, electrode 215 may be on the exterior wall of cannula 215 (e.g., a tubular outer lead 206), or in the middle between the interior and exterior walls of cannula 215. One way to form lead 206 about the interior wall of cannula 215 is to extrude a polymer on the tubular lead (e.g., via a cross-head extrusion die). One way to form lead 206 about the exterior wall of cannula 215 is by winding a conductive material (e.g., insulated wire) on cannula 215 (e.g., using cannula 215 as a mandrel). One way to form lead 206 between the interior and exterior walls of cannula 215 is to extrude an inner portion of cannula 215 (e.g., by winding); locate lead 206 on the inner portion of cannula 215; and extrude an outer portion of cannula 215 on the combined inner portion and lead. It is appreciated that in the embodiment shown in FIG. 6, lead 206 need not be a continuous tubular structure, instead, lead 206 may be a strand of a conductive material (e.g., wire) that is connected to electrode 214 as an annular ring.

FIG. 7 shows another embodiment of distal end 210 of first lead 206 and cannula 215. Distal end 210 includes first electrode 214 on one side and second electrode 230 on another side of distal end 210 of lead 206. First electrode 214 and/or second electrode 230 may be located on the interior wall of cannula 215 adjacent to lumen 212, on the exterior wall of cannula 215, or in the middle between the interior and exterior walls of cannula 215. Separately positioned electrodes may be formed, in one embodiment by winding two conductive materials (e.g., two leads in a tubular configuration on, in, or within cannula 215). In this embodiment, there is lumen 212 running through cannula 215 that creates an annular space that can be used for the storage and/or delivery of a liquid and/or a solid treatment agent.

Another embodiment is shown in FIG. 8. In this embodiment, distal end 210 of first lead 206 is shown with lumen 212 therethrough that defines an annular space. In lumen 212 there is disposed first electrode 214 and second electrode 230. One way this configuration may be formed is by winding two leads (e.g., lead 206 and another lead) about a mandrel to form a tubular structure then extruding a polymer over the tubular structure to define lumen 212. The annular space of lumen 212 may be used for the storage and/or delivery of a liquid and/or a solid treatment agent.

Figure 9:
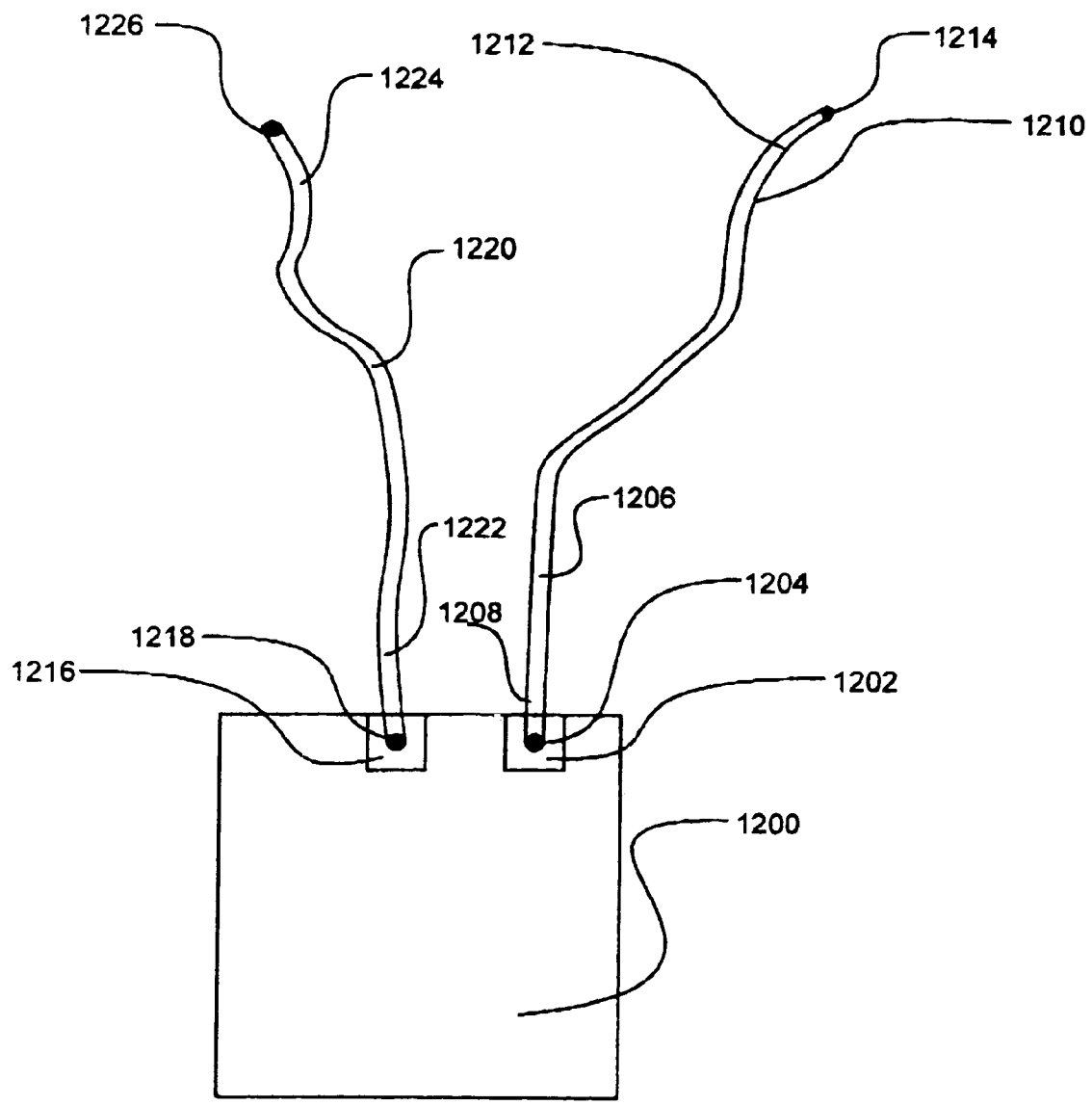
FIG. 9 schematically illustrates a device having two leads with an electrode on the distal end of each lead.

Another embodiment of a device that may be used for stimulative angiogensis is shown by FIG. 9. Device 1200 is shown with multiple leads, in this example two leads, first lead 1206 and second lead 1220 attached to device 1200. First lead 1206 is connected to first electrical output channel 1202. Device 1200 includes a housing that may contain a power source and an electronic circuitry to generate and send, respectively, electrical energy signals (e.g., pulses) to one or both of first lead 1206 and second lead 1220.

First lead 1206 includes proximal end 1208 shown connected by first connection 1204 to first electrical output channel 1202. First lead 1206 also includes distal end 1210 and electrode 1214. Cannula 1212 having a lumen therethrough may also be included at distal end 1210 of first lead 1206 for the purpose of running electrode 1214 therethrough, running a second electrode (not shown) therethrough, or storing, or providing a conduit for a treatment agent. The housing of device 1200 may, for example, include a first reservoir to store a suitable predetermined volume of a treatment agent that can be delivered through cannula 1212.

Device 1200 also is shown with second lead 1220 connected to device 1200. Second lead 1220 is connected to second electrical output channel 1216 by second connection 1218. Second lead 1220 includes proximal end 1222 adjacent to second connection 1218. Second electrical output channel 1216 may be coupled to the electronic circuitry and the power source. Second lead 1220 also includes distal end 1224 which is shown with electrode 1226. First electrical output channel 1202 and/or second electrical output channel 1216 provide, in one embodiment, a sub-threshold voltage, an above-threshold voltage, and/or a defibrillation voltage. Second lead 1220 may be disposed in a cannula having a lumen therethrough for storing or providing a conduit for a treatment agent. The housing may also include a second reservoir to store a suitable predetermined volume of treatment agent that can be delivered through the optional cannula about second lead 1220. The second reservoir may be the same (where similar treatment agents are to be delivered through different cannulas) or different (where different treatment agents are to be delivered through different cannulas) than the first reservoir.

Although device 1200 in FIG. 9 is shown with first lead 1206 and second lead 1220 connected to device 1200, device 1200 can be manufactured, packaged, and sold without first lead 1206, or second lead 1220 connected to device 1200. In order for device 1200 to be operational, one or more leads must be connected to device 1200.

Distal end 1210 of first lead 1206 and/or distal end 1224 of second lead 1220 may be, in one embodiment, as illustrated by FIGS. 4-8. It is envisioned that the reference numerals referring to distal end 1210 of first lead 1206 in FIGS. 4-8 can be adjusted, as appropriate, to refer to distal end 1224 of second lead 1220.

Figure 10:
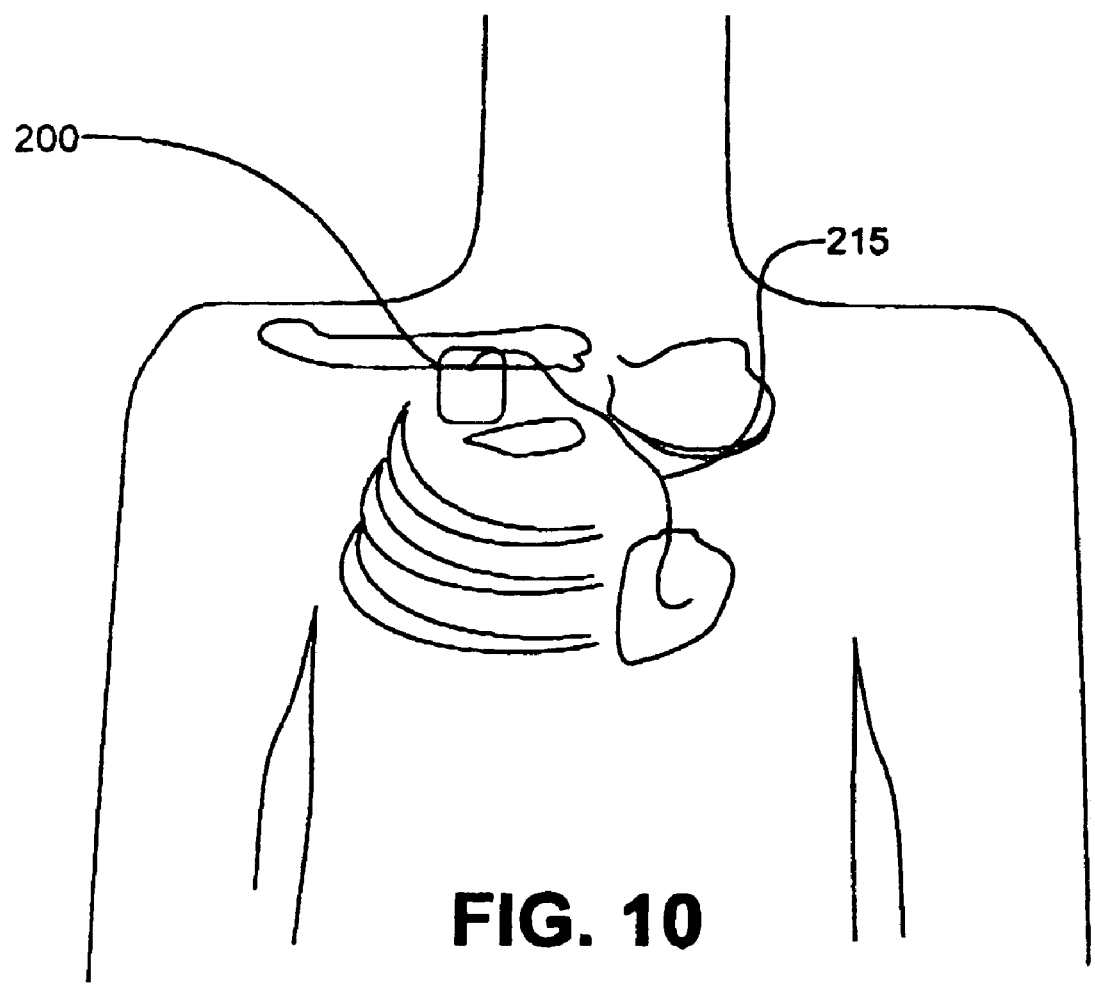
FIG. 10 schematically illustrates the implantation of a device in a patient.

FIG. 10 schematically illustrates a device such as device 200 or device 1200 implanted in a human subject. Referring to device 200, in one embodiment, device 200 is implanted in a manner similar to a pacemaker or a defibrillator. Using, for example, an embodiment of the device shown in FIG. 3, housing 201 is placed below a subject's chin adjacent the clavicle. One or more leads extend from the device housing to the exterior of the subject's heart. Referring to device 200 (shown in FIG. 3), distal end of lead 210 and/or distal end 217 (of cannula 215) may extend to a location on the exterior of the heart. In another embodiment, device 200 is outside the patient's body, and one or more leads 206, 1206, and/or 1220 are fed into patient, for example, percutaneously. In one embodiment, leads 206, 1206, and/or 1220 have a length of about 75-100 cm, and in another embodiment, a length of about 25-75 cm.

FIG. 11 illustrates a magnified view of the sternocostal surface of the exterior of the human subject's heart depicted in FIG. 10. FIG. 12 illustrates a magnified view of the diaphragmatic surface of the exterior of the human subject's heart depicted in FIG. 10. Notably, FIGS. 11 and 12 illustrate the vasculature 150 on the exterior of the heart. The venous system is typically made up of coronary sinus 242, great cardiac vein 244, posterior veins of left ventricle 246, middle cardiac vein 250, small cardiac vein 252, anterior intraventricular vein 248, anterior cardiac veins of right ventricle 268, and oblique vein of left atrium 272. Coronary sinus 242 drains into right atrium 262. Middle cardiac vein 250, small cardiac vein 252, posterior veins of left ventricle 246, great cardiac vein 244, oblique vein of left atrium 272, all drain into coronary sinus 242. Anterior interventricular vein 248 drains into great cardiac vein 244 which drains into coronary sinus 242.

Referring to FIGS. 11 and 12, the coronary artery network includes right coronary artery 180 and left coronary artery 162. Left main coronary artery 162 branches off into circumflex branch of left coronary artery 170 and left anterior descending artery 160. Anterior interventricular branch of left coronary artery 160 feeds interventricular septal branches 164. Circumflex branch of left coronary artery 170 feeds posterior left ventricular branch 168. Right coronary artery 180 feeds atrial branch of right coronary artery 182, right marginal branch of right coronary artery 166, posterior interventricular branch of right coronary artery 174, and interventricular septal branches 172. Other parts of the coronary artery network include sinuatrial nodal branch 176 adjacent to sinuatrial node 178.

In one embodiment, lead 206 is fed into the coronary sinus 242 from right atrium 262, which can be accessed from the superior or inferior vena cava. Once lead 206 is in the coronary sinus, distal end 210 and electrode 214 and cannula 215 with lumen 213 may be placed in middle cardiac vein 250 (as shown), anterior intraventricular vein 248, the posterior vein of left ventricle 246, great cardiac vein 244, or another vein as necessary to treat an ischemic area of the patient's heart. A treatment agent may then be delivered into one of these veins through lumen 212. In addition, one or more of a sub-threshold, above threshold, or defibrillator voltage may be delivered to electrode 214, which may also be placed in the problem area.

In one embodiment, a therapeutic angiogenic response is induced and modulated by locally delivering a treatment agent (optionally in a sustained-release carrier) to an ischemic region or area in combination with an electrical voltage. This combination of a treatment agent with an electrical voltage will be referred to for simplicity as "treatment" (in this embodiment). The treatment may be strategically placed, for example, adjacent to or along an occlusion to produce an angiogenic concentration gradient to encourage the specific directional growth or expansion of collateral vessels. For example, in reference to FIGS. 2 and 11, treatment placed in great cardiac vein 244, adjacent to zone 190A of occluded vessel LCX 170 are selected such that, while upstream, a therapeutic angiogenic or arteriogenic response will encourage growth of collaterals around occlusion 185 meeting up with LCX 170 downstream of the occlusion. In FIG. 11, representative treatment is shown (in the inset) at site 257. Treatment may be placed along the path to encourage growth along a desired path. In terms of electrical stimulation, in one embodiment, electrode 214 is in contact with the blood vessel wall (e.g., the wall of great cardiac vein 244) adjacent site 190A. Similarly, a treatment strategically placed at a location in or near anterior interventricular branch of left coronary artery 160 (e.g., in anterior interventricular vein 248 adjacent to region 190B) will encourage bridging of collateral vessels, in this case, at site 190B between anterior interventricular branch of left coronary artery 160 and LCX 170. Similar encouragement and bridging may be obtained by strategically placing a treatment at a region of RCA 180 (such as in middle cardiac vein 250 adjacent to region 190C). A device such as device 1200 (FIG. 9) may be suitable in a situation where it is desired to place multiple leads and deliver treatment agent or agents to multiple sites to stimulate bridging (e.g., placing one lead/lumen at great cardiac vein 244 and another at middle cardiac vein 250).

Suitable treatment agents and methods and devices for their application are disclosed in co-pending application Ser. No. 10/011,071, filed on Nov. 30, 2001, which is herein incorporated by reference in its entirety.

Suitable treatment agents include specific binding or receptor binding treatment agents. Suitable sustained-release carriers may take the form of nanoparticles or microparticles, typically in the form of nanospheres or microspheres, having an average particle size with an average diameter less than 100 microns (μm) and preferably up to about a 10 μm (and preferably less than 10 microns). Treatment agents that can sustain their effectiveness (e.g., through the use of a sustained-release carrier) for a period of up to one to ten weeks, preferably up to two to eight weeks are believed to offer maximum benefit for the stimulation of therapeutic angiogenesis. In another embodiment, treatment agents that can sustain their effectiveness for one day or longer may be used.

In another embodiment, suitable treatment agents may include small molecules, proteins, and genes. In one embodiment, the small molecules, proteins, and genes may sustain release compositions. One example includes delivering a treatment agent that is a gene or genes in a cell. The small molecules, proteins, and genes are discussed in more detailed in co-pending U.S. patent application Ser. No. 10/011,071, referenced above.

Referring to FIGS. 3 and 11, electrical output channel 202 of device 200 may deliver a sub-threshold voltage. The delivered sub-threshold voltage may take the form of intermittent pulses, for example, pulses at predetermined time intervals controlled by electronic circuitry 218. In another embodiment, the sub-threshold voltage of first electrical output channel 202 has a waveform. Suitable waveforms include sinusoidal, block, exponential decay, polynomial, power function, linear function, alternating current, direct current, step and combinations thereof.

The embodiment described above with reference to FIGS. 3 and 11-12 involved device 200 having a lead with a single electrode 214. In another embodiment, lead 206 may include multiple electrodes. For example, multiple electrodes may be placed along a lead to stimulate a treatment along a desired path that lead 206 follows or crosses. One way this may be done is constructing a lead as an insulated conductive material (wire) with an exposed portion of the conductive material at desired treatment sites. One embodiment where a device such as device 1200 with multiple leads (FIG. 9), one or more of which may include a conduit for delivery of a treatment agent, may be used, is placement of the leads at desired points along a path for which therapeutic angiogenesis may be desired. This technique was described above with reference to FIGS. 11 and 12 and positioning leads at sites 190A and 190B (see FIG. 2).

In another embodiment, a method for stimulating angiogenesis includes positioning electrode 214 on lead 206 at a location in a blood vessel; connecting lead 206 to electrical output channel 202 adapted to deliver a sub-threshold voltage; activating electrical output channel 202 to deliver the sub-threshold voltage through lead 206 to electrode 214; actuating pump 232; and delivering a treatment agent adapted to stimulate angiogenesis at a location in the blood vessel. In one embodiment, the location where the treatment agent is delivered is the same location where the electrode is located. In another embodiment, the location where the treatment agent is delivered is at a different location in the same or a different blood vessel than the position of electrode 214 on lead 206. One way that the location where the treatment agent is delivered may be different from the position of the electrode is through the use of a cannula (e.g., connected to reservoir 228) for the treatment agent that is separate from lead 206. Alternatively, lead 206 may be of a length different than the length of cannula 215. For example, lead 206 may be significantly longer than cannula 215 so that electrode 214 is positioned further along a blood vessel path than cannula 215.

With reference to FIG. 9 and an embodiment of a device with multiple leads, in another embodiment, a method also includes positioning second electrode 1226 on second lead 1220 at a location in a blood vessel; connecting second lead 1220 to second electrical output channel 1216 adapted to deliver an above-threshold voltage; and activating second electrical output channel 1216 to deliver the above-threshold voltage through second lead 1220 and second electrode 1226 to stimulate heartbeats. For example, second lead 1220 may be one of possibly multiple leads positioned about a subject's heart to deliver electrical energy in the form of pulses to stimulate heartbeats according to a desired rhythm. First lead 1210 (and optional delivery cannula) may be positioned at a region to stimulate therapeutic angiogenesis, for example, adjacent an occlusion. An electrical energy stimulus (e.g., pulse) may be delivered through electronic circuitry 1218, for example, between heartbeat stimulus signals.

Referring again to FIG. 9 and an embodiment of a device having multiple leads, in another embodiment, a method also includes activating one of either first electrical output channel 1202 and/or second electrical output channel 1216 to deliver a voltage sufficient to achieve electroporation to facilitate delivery of the treatment agent. The voltage is delivered through one of either first lead 1206 and/or second lead 1220 to at least one of first electrode 1214 and/or second electrode 1226 (shown in FIG. 9) and/or first electrode 214 and/or second electrode 230 (shown in FIGS. 7 and 8). If transport of the treatment agent into cells is desired, an electric field may be applied to cause electroporation. Electroporation is a temporary condition of an outer membrane of a target cell becoming "porous" as a result of high electric field. While the cells are porous due to the electric field, the treatment agent can be efficiently delivered into the cell.

In another embodiment, method also includes positioning second electrode 1226 on second lead 1220 at a second location in a blood vessel, connecting second lead 1220 to second electrical output channel 1216, and activating first electrical output channel 1202 and/or second electrical output channel 1216 to create a current field to facilitate delivery of the treatment agent by iontophoresis. Iontophoresis is a current-facilitated transport of charged entities such as ions, molecules, proteins, particles away from an electrode that has charge opposite to that of the given entity (for example, a positively charged electrode will drive transport through the tissue of the negatively charged entity).

Figure 13:
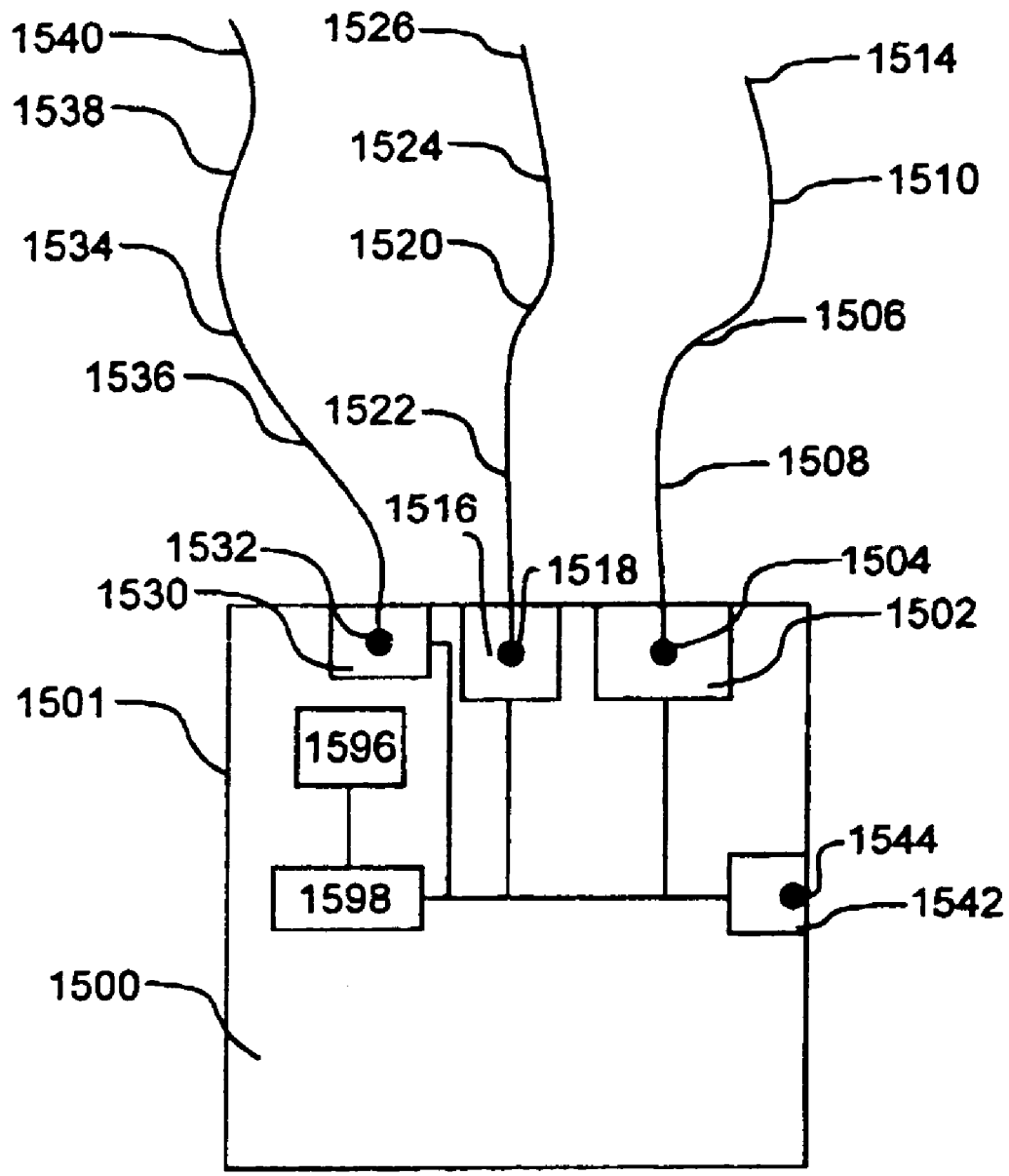
FIG. 13 schematically illustrates a device having a lead with an electrode on the distal end of the lead.

Referring now to FIG. 13, a device that may be used for stimulating angiogenesis is illustrated. Device 1500 may be similar in size to modem pacemakers and defibrillators. Representatively, device 1500 includes housing 1501 that contains power source 1596, and electronic circuitry 1598 to generate signals (pulses) and control the timing of the electrical energy and the amount of energy delivered. Electronic circuitry 1598 includes, for example, a processor containing machine readable program instructions enabling electronic circuitry 1598 to generate and control the timing of electrical energy to multiple leads. Device 1500 includes first electrical output channel 1502 (coupled to power source 1596 and/or circuitry 1598) connected to first lead 1506 by first connection 1504. In one embodiment, first connection 1504 is, for example, a pinch type connection. In order to energize first lead 1506, first connection 1504 between first lead 1506 and device 1500 must be made, but device 1500 can be packaged and sold without first connection 1504 having been made.

Device 1500 may also optionally include second electrical output channel 1516 connected to second lead 1520 and second connection 1518. Also, device 1500 may optionally include third electrical output channel 1530 connected to third lead 1534 and third connection 1532. Device 1500 may also optionally include fourth electrical output channel 1542 with electrode 1544 on outside of housing 1501.

First lead 1506 includes proximal end 1508 adjacent to connection 1504 and distal end 1510. Distal end 1510 includes first electrode 1514. First electrode 1514 delivers electrical energy from first electrical output channel 1502. Optional second lead 1520 includes proximal end 1522 adjacent to connection 1518 and distal end 1524. Distal end 1524 includes second electrode 1526. Optional third lead 1534 includes proximal end 1536 adjacent to third connection 1532. Optional third lead 1534 also includes distal end 1538, having third electrode 1540.

In one embodiment, device 1500 may be used for treatment where electrical stimulation is applied to the heart. Distal end 1510 of first lead 1506 may be placed in one of the right atrium, the right ventricle, the left ventricle wall, or the venous system on the exterior of the heart. In one embodiment, first electrode 1514 delivers only a sub-threshold pacing voltage. In another embodiment, first electrode 1514 delivers only an above-threshold pacing voltage. In another embodiment, first electrode 1514 delivers an above-threshold pacing voltage, and a sub-threshold voltage during the refractory period after the pacing voltage pulse. In this embodiment, circuitry 1598 creates a modified waveform at a pacing voltage to have a pacing and a therapeutic angiogenic effect. In one embodiment, a sub-threshold voltage is delivered about 100 to 200 milliseconds after the pacing voltage pulse.

In another embodiment, first lead 1506 and/or optional second lead 1520, optional third lead 1534, respectively, having first electrode 1514, second electrode 1526 and third electrode 1540, may be used to deliver a voltage to heart. In another embodiment, optional fourth electrode 1544 can also be used. First electrode 1514, second electrode 1526, and third electrode 1540 may be placed in one or more of the right atrium, the right ventricle, the left ventricle wall, and the venous system on the exterior of the heart. First electrode 1514, optional second electrode 1526, optional third electrode 1540, and/or optional fourth electrode 1544 may be used to deliver an above-threshold voltage, a sub-threshold voltage, or both an above-threshold voltage and a sub-threshold voltage in a modified waveform at the same time.

Figure 14:
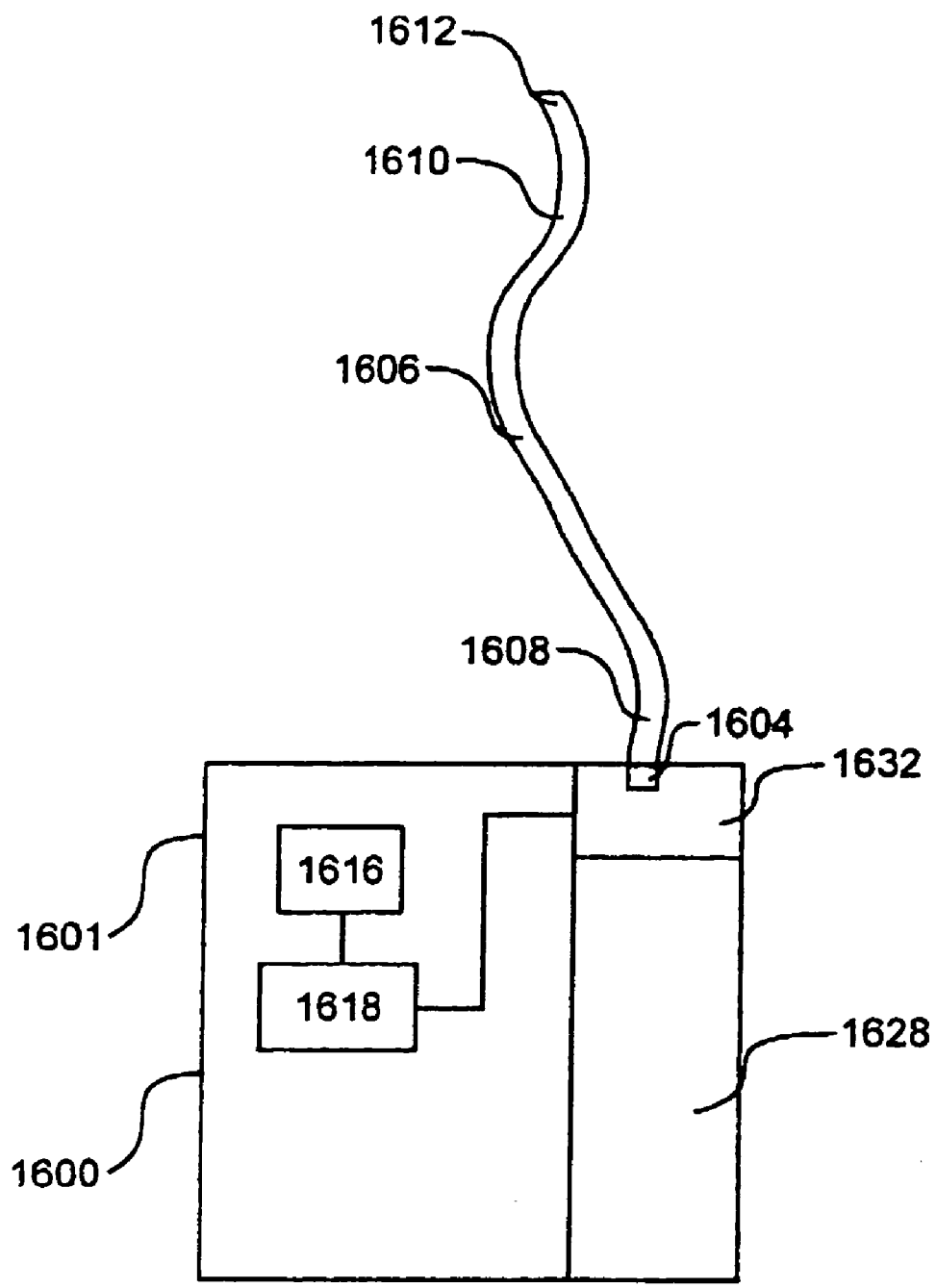
FIG. 14 schematically illustrates a device having a catheter.

FIG. 14 schematically illustrates an alternative embodiment of a device in the form of device 1600. Device 1600 includes housing 1601, power source 1616, and electronic circuitry 1618. Reservoir 1628 may contain, for example, a liquid that includes one or more treatment agents. Connected to reservoir 1628 is pump 1632. Pump 1632 has connection 1604 to liquid delivery cannula 1606. Cannula 1606 has proximal end 1608 adjacent to connection 1604 and distal end 1610. One or more cannula openings 1612 are adjacent to distal end 1610. Optionally, one or more other delivery cannulas (not shown) may be connected to device 1600. Electronic circuitry 1618 includes a processor and machine readable program instructions for the delivery of a treatment agent (timing and amount/volume) from pump 1632 through cannula 1606.

In one embodiment, openings 1612 at distal end 1610 of cannula 1606 may be placed in the venous system on the exterior of the heart, for example, openings 1612 may be fed into coronary sinus 242 and into great cardiac vein 244, posterior vein of left ventricle 246, middle cardiac vein 250, small cardiac vein 252, anterior intraventricular vein 248, anterior cardiac vein of right ventricle 268, or oblique vein of left atrium 272 (shown in FIGS. 11 and 12). Once openings 1612 are in place in the correct vein on the exterior of the heart, pump 1632 may be activated to force a treatment agent from reservoir 1628 through pump 1632 through cannula 1606 to openings 1612 into the vein. The liquid may include one or more treatment agents.

In another embodiment, pump 1632 and reservoir 1628 are not needed since a treatment agent(s) may be coated on the exterior of cannula 1606 or loaded into distal end 1610 of cannula 1606 so that treatment agent(s) may elute off cannula 1606 and into the blood vessel (e.g., vein). Generally, for a sustained release material to be effective, distal end 1610 or cannula 1606 must fully occlude the blood vessel, so that sustained release material cannot be washed out by the normal blood flow through the blood vessel.

Figure 15:
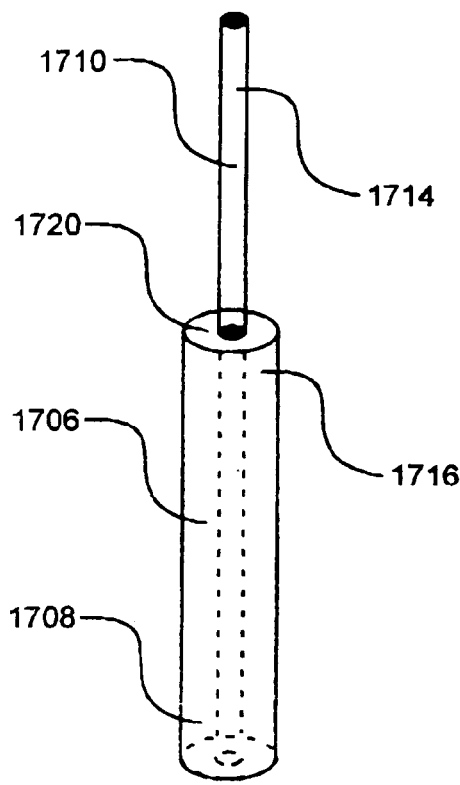
FIG. 15 schematically illustrates a lead having an electrode at the distal end of the lead.
Figure 16:
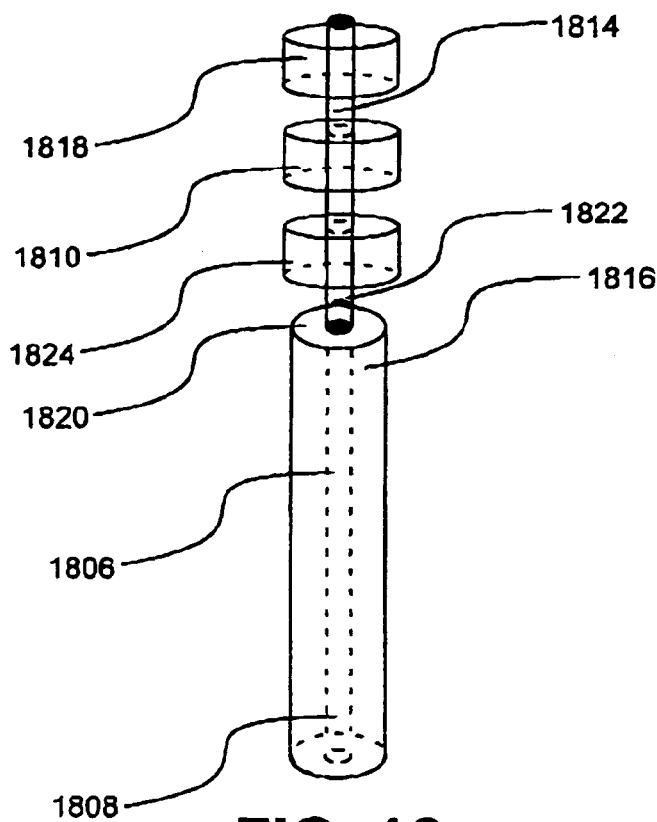
FIG. 16 schematically illustrates a lead having an electrode at the distal end of the lead.

Referring now to FIGS. 15 and 16, leads 1706 and 1806 can be used with device 200 (FIG. 3), device 1200 (FIG. 9), device 1500 (FIG. 13), and device 1600 (FIG. 14).

FIG. 15 illustrates lead 1706 having proximal end 1708 adapted to connect to an electric output channel (not shown) and distal end 1710. At distal end 1710 is electrode 1714. Lead 1706 includes insulating material 1716 surrounding electrode 1714 until desired point 1720 on distal end 1710. Distal to insulating material 1716, electrode 1714 can transmit electrical signals or pulses to its surroundings.

FIG. 16 illustrates lead 1806 having proximal end 1808 adapted to connect to an electrical output channel (not shown), and distal end 1810. Distal end 1810 includes electrode 1814 and sections of insulating material 1818. Sections of insulating material 1818 allow for exposed portions 1822 and unexposed portions 1824 of electrode 1814. Insulating material 1816 covers electrode 1814 until desired point 1820 at distal end 1810.

In one embodiment, electrodes 1714 and/or 1814 are about 2-5 mm in length. In another embodiment, the length of electrodes 1714 and/or 1814 may be adjusted to get the desired lead impedance.

In one embodiment, lead 1706 and/or lead 1806 can be used in conjunction with device 200 shown in FIG. 3, for example to facilitate treatment agent delivery to a desired region, or for example, iontophoresis. In one embodiment, first lead 206 (see FIG. 2) may be fed into a blood vessel, for example, posterior vein of left ventricle 246 (shown in FIG. 12). Second lead 1706 or 1806 can be fed into another blood vessel, for example, middle cardiac vein 250 (shown in FIG. 12). Once first lead 206 and second lead 1706 or 1806 are in place, pump 232 can be activated to force a treatment agent from reservoir 228 through pump 232 to distal end 217 of cannula 215 and be forced into posterior vein of left ventricle 246. Simultaneously, electronic circuitry 218 delivers electrical energy to first lead 206 and/or second lead 1706 or 1806 creates a field between first electrode 214 on first lead and second electrode 1714 or 1814 (for example, exposed portions 1822 of electrode 1814 in middle cardiac vein 250). The voltages create an iontophoresis filed, or a voltage gradient for the transportation of the drugs or treatment agents from posterior vein of left ventricle 246 to middle cardiac vein 250, in order to treat posterior interventricular branch of right coronary artery 174. One way an electric field may be created is by delivering electrical energy in the form of oppositely charged current (e.g., first electrode sees a positive charge and second electrode 1714 or 1814 a negative charge. In another embodiment, second lead 1706 is used, which only has one section of exposed electrode 1714 at distal end 1710; in this embodiment with second lead 1706, a more concentrated and focused iontophoresis field can be created. In one embodiment, a voltage of about 5-10 volts is applied to create an iontophoresis field. In another embodiment, a pulsed voltage may be used to prevent fibrillation.

Figure 17:
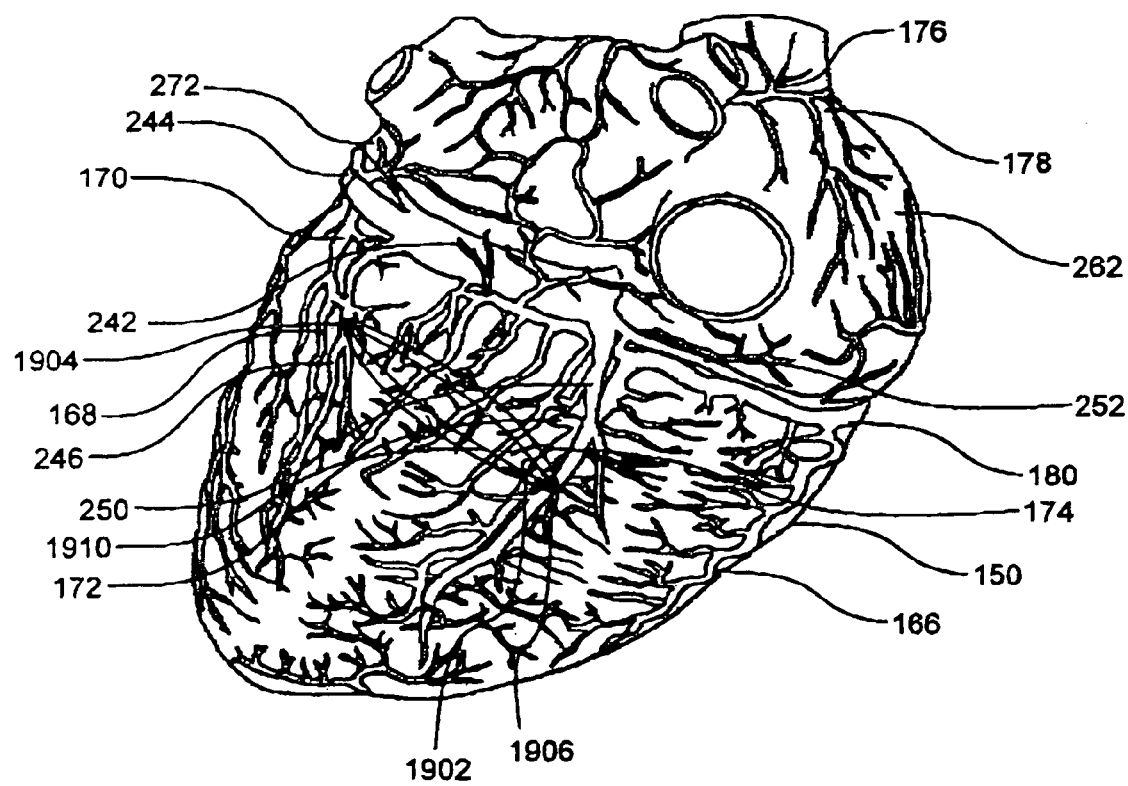
FIG. 17 schematically illustrates the coronary arteries and cardiac veins on the diaphragmatic surface on the exterior of the heart showing an electric field.

In another embodiment, a method of treating a problem area 1902 in posterior interventricular branch of right coronary artery 174 is shown in FIG. 17. At area 1904 in posterior vein of left ventricle 246, an electrode and at least one treatment agent are introduced. At area 1906 in middle cardiac vein 250, at least one electrode is introduced. When a voltage is applied to electrodes in areas 1904 and 1906, electric field 1910 is created to force treatment agent to problem area 1902. Representatively, the treatment agent flows toward problem area 1902 and thereby contacts branching arteries which, for example, stimulate the growth of one or more arteries, thus inducing an arteriogenesic effect.

Figure 18:
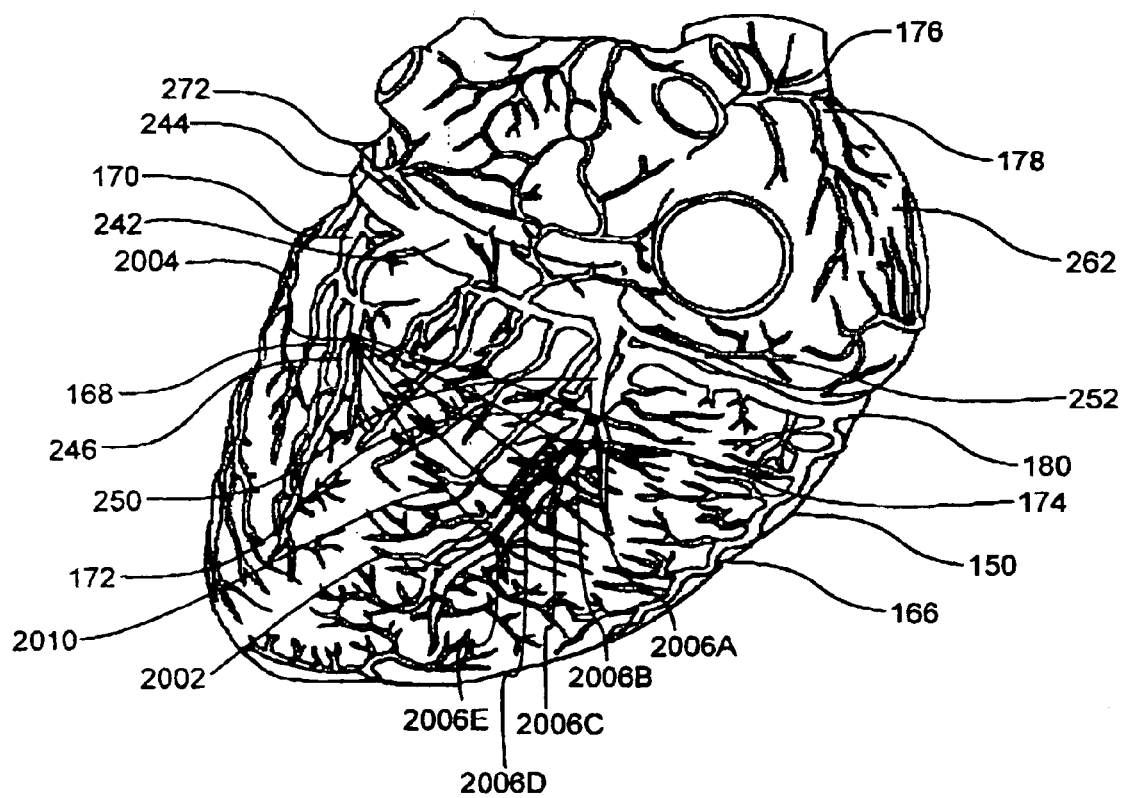
FIG. 18 schematically illustrates the coronary arteries and cardiac veins on the diaphragmatic surface on the exterior of the heart showing an electric field.

In another embodiment, as shown in FIG. 18, a method of treating problem area 2002 in posterior interventricular branch of right coronary artery 174 is shown. A first electrode and a drug or treatment agent are introduced at area 2004 in posterior vein of left ventricle 246. A plurality of electrodes are located in areas 2006A, 2006B, 2006C, 2006D and 2006E in middle cardiac vein 250. When a voltage is applied to first electrode at area 2004 and a different voltage is applied to one or more of a second set of electrodes at areas 2006A, 2006B, 2006C, 2006D, and 2006E, electric field 2010 is created to force treatment agent(s) to problem area 2002 in posterior interventricular branch of right coronary artery 174.

In another embodiment, as shown in FIG. 17, only an electrode and not a treatment agent or agents is introduced to area 1904, and only an electrode is introduced to area 1906, to create electric field 1910 across problem area 1902.

In another embodiment, as shown in FIG. 18, only an electrode is introduced to area 2004 and not a drug or treatment agent, and electrodes are introduced to areas 2006A, 1006B, 2006C, 2006D, and 2006E, so that when a voltage difference is applied across at least two of the electrodes, electric field 2010 is created across problem area 2002.

The methods described in conjunction with FIGS. 17 and 18 can be used for iontophoretic delivery, or electroporation delivery of a treatment agent. Generally, an electroporation delivery voltage will be higher than an iontophoretic delivery voltage. Also, an electroporation delivery voltage will be relatively higher than an angiogenic sub-threshold voltage. Iontophoresis is generally used to deliver a treatment agent into the general area of cells, while electroporation is used to send a drug or treatment agent into the cell. Electroporation may be used to temporarily open holes in the cell membrane so that molecules, drugs or other entities can flow into or out of cells depending on concentration gradients. In one embodiment, an electroporation voltage is at least about 75 volts.

Figure 19:
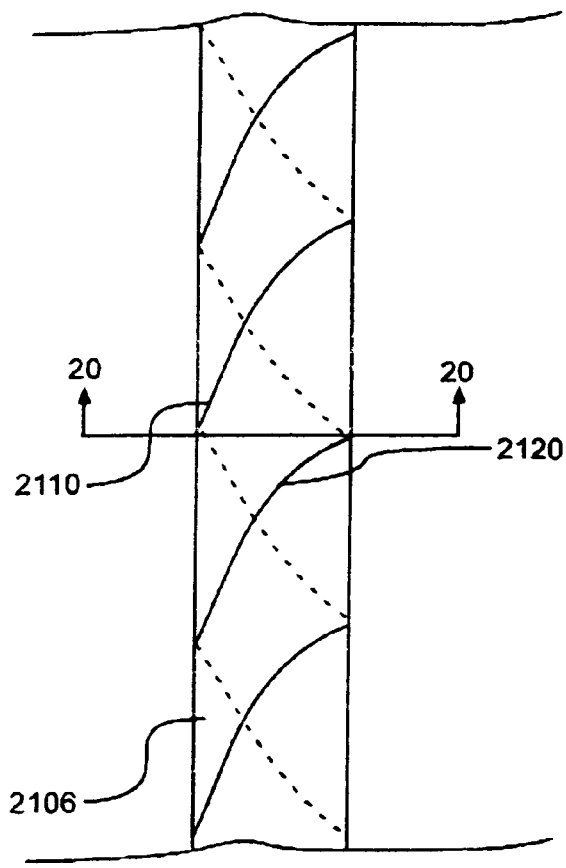
FIG. 19 schematically illustrates a portion of a lead having a plurality of electrodes.

Referring now to FIG. 19, which schematically illustrates lead 2106 which may be used with device 200, 1200, 1500, and/or 1600 to replace one or more of leads 206, 1206, 1220, 1506, 1520, 1534, and/or 1606. A portion of lead 2106 is shown which has first conductor 2110 and optional second conductor 2120 wrapped in a helical fashion about exterior of lead 2106. Conductor 2110 electrically connects an electrode, positioned on the surface of the lead near the distal end to a terminal pin (not shown) on the proximal end of the lead to permit the passage of current between a device output channel and the electrode. In a similar way, conductor 2120 may be connected to a separate distal electrode and proximal terminal pin (not shown).

Figure 20:
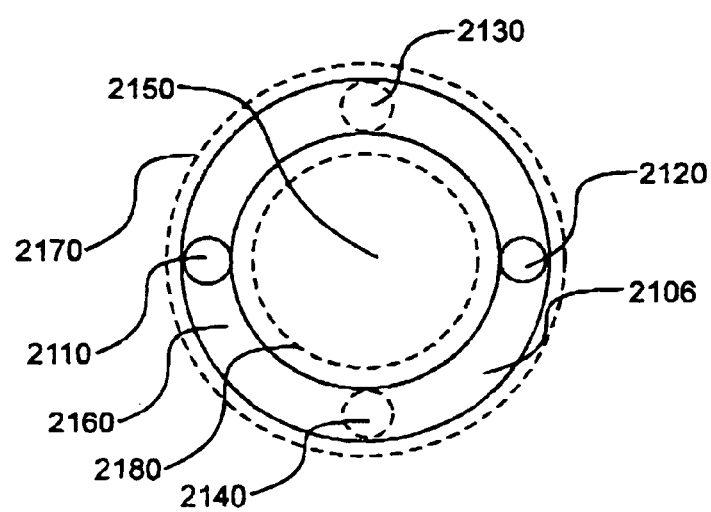
FIG. 20 schematically illustrates a cross-section of the lead of FIG. 19.

A cross-sectional view of lead 2106 taken along line 20-20 is illustrated in FIG. 20. FIG. 20 illustrates lead body 2106 having first conductor 2110 in matrix 2160. Optional second conductor 2120, third conductor 2130, and fourth conductor 2140 are also shown. First conductor 2110 and optional second conductor 2120, third conductor 2130, and fourth conductor 2140 may either be fed straight along lead 2106 or wrapped in a helical fashion about lead body 2106. First conductor 2110 and optional second conductor 2120, third conductor 2130, and fourth conductor 2140 are disposed within matrix 2160. Matrix 2160 is made of a material, for example, a polymer. Lumen 2150 is provided interior to matrix 2160 and one or more conductors 2110, 2120, 2130, and 2140. Optionally, one or more layers of inner liner 2180 may be provided interior to matrix 2160 and one or more conductors 2110, 2120, 2130, and 2140, and exterior to lumen 2150. Also, one or more outer layers 2170 may be provided exterior to matrix 2160 and one or more conductors 2110, 2120, 2130, and 2140. In one embodiment, conductors may be co-extruded with lead body 2106.

Although devices 200, 1200, 1500, and 1600 have been described to be used in an ischemic region for angiogenesis, devices can also be used following myocardial infarction. For example, following a myocardial infarction, other areas of the heart are at risk, and a treatment could be applied to the risk areas to provide angiogenic or arteriogenic treatment to these risk areas. Generally, such treatment will be delivered to tissue near the infarct area or to areas of the heart that did not suffer an infarct, for example to an area undergoing remodeling following the infarct. Also, following myocardial infarction in the heart, other areas of the heart that did not suffer the infarction may undergo hypertrophy, or cell enlargement. These areas of the heart undergoing hypertrophy could use treatment from device 200, 1200, 1500, or 1600 to increase blood flow to these areas since the larger myocytes need more blood flow. The devices and methods described are also applicable to the treatment of flow limiting obstructions in other coronary vessels and in the peripheral vasculature.

Having disclosed exemplary embodiments and the best mode, modifications and variations may be made to the disclosed embodiments while remaining within the scope of the invention as defined by the following claims.

The invention claimed is:

1. A method for stimulating angiogenesis, comprising:
    positioning a first electrode on an implantable first lead at a first intravascular location;
    connecting the first lead to an implantable first electrical output channel adapted to deliver a sub-threshold voltage such that the first electrode is electrically connected to the first electrical output channel, the sub-threshold voltage below a threshold voltage required to cause a local depolarization of cardiac myocyte cell membranes;
    activating the first electrical output channel to deliver the sub-threshold voltage through the first lead to the first electrode; and
    delivering a treatment agent adapted to stimulate therapeutic angiogenesis at the first intravascular location via an implantable cannula including a lumen configured to deliver a liquid or solid treatment agent to a distal end of the first lead, wherein the first lead includes at least a portion disposed within the lumen and has an outer diameter that is smaller than an inner diameter of the cannula to form an annular space suitable for flow of the liquid or solid treatment agent;
    wherein the first lead is adapted to deliver the sub-threshold voltage and one or more of pacing or defibrillation voltages to the first electrode.

2. The method of claim 1, further comprising positioning a second electrode on a second lead at a second intravascular location;
    connecting the second lead to a second electrical output channel adapted to deliver an above-threshold voltage; and
    activating the second electrical output channel to deliver the above-threshold voltage through the second lead and to the second electrode to stimulate heart beats.

3. The method of claim 1, further comprising activating the first electrical output channel to deliver a voltage sufficient to achieve electroporation to facilitate delivery of the treatment agent, wherein the voltage is delivered through the first lead to the first electrode at the first intravascular location.

4. The method of claim 1, further comprising activating the first electrical output channel to deliver at least one of an above-threshold stimulation for pacing and an above-threshold stimulation for pre-excitation through the first lead to the first electrode at the first intravascular location.

5. The method of claim 1, further comprising positioning a second electrode on a second lead at a second intravascular location;
    connecting the second lead to a second electrical output channel; and
    activating the first and second electrical output channels to create an electrical field to facilitate delivery of the treatment agent by iontophoresis.

6. The method of claim 1, further comprising positioning a second electrode on a second lead at a second intravascular location;
    connecting the second lead to a second electrical output channel; and
    activating the first and second electrical output channels to create an electrical field to facilitate delivery of the treatment agent by iontophoresis and cellular uptake by electroporation.

7. The method of one of claims 1, 3, or 4, further comprising a second electrode positioned on the first lead adjacent to the first electrode.

8. The method of claim 5, further comprising activating at least one of the first and second electrical output channels to deliver an above-threshold stimulation for at least one of pacing and pre-excitation through the first lead to the first electrode at the first intravascular location.

9. A method for stimulating angiogenesis, comprising:
    delivering a sub-threshold voltage to a location in a blood vessel through an implantable lead having an electrode positioned in the blood vessel, wherein the lead is connected to an implantable electrical output channel adapted to deliver a sub-threshold voltage to the electrode, the sub-threshold voltage below a threshold voltage required to cause a local depolarization of cardiac myocyte cell membranes; and
    delivering a treatment agent adapted to stimulate therapeutic angiogenesis at the location via an implantable cannula including a lumen configured to deliver a liquid or solid treatment agent to a distal end of the lead, wherein the lead includes at least a portion disposed within the lumen and has an outer diameter that is smaller than an inner diameter of the cannula to form an annular space suitable for flow of the liquid or solid treatment agent; and
    wherein the lead is adapted to deliver the sub-threshold voltage and one or more of pacing or defibrillation voltages to the electrode.

10. The method of claim 1 or 9, wherein the sub-threshold voltage is less than about 1.0 volts.

11. The method of claim 1 or 9, wherein the sub-threshold voltage is less than about 0.75 volts.

12. The method of claim 1 or 9, wherein the sub-threshold voltage is less than about 0.5 volts.

13. The method of claim 1 or 9, wherein the sub-threshold voltage is less than about 0.1 volts.

14. The method of claim 1 or 9, wherein the distal end of the lead is located in a coronary sinus, a great cardiac vein, a posterior vein of the left ventricle, an anterior interventricular vein, a middle cardiac vein, or any other vein of sufficient size to place the first lead.

15. The method of claim 1 or 9, wherein the treatment agent is selected from the group consisting of poly (L-lactide), poly (D, L-lactide), poly (glycolide), poly (lactide-co-glycolide), polycaprolactone, polyanhydride, polydiaxanone, polyorthoester, polyamino acids, poly (trimethylene carbonare), bioresorbable inorganic compound, fibrin, gelatin, chitin, a bacterial polysaccharide, a metal, polyhydroxybutyratevalerate, a poly(oxy)ethylene, a polyurethane, a silicone, and combinations thereof.

16. The method of claim 1 or 9, wherein the treatment agent is selected from the group consisting of vascular endothelial growth factor, fibroblast growth factor, monocyte chemoattractant protein 1, transforming growth factor beta, transforming growth factor alpha, lipid factor, hypoxia-inducible factor 1-alpha, PR39, DEL 1, nicotine, insulin-like growth factor, placental growth factor, hepatocyte growth factor, estrogen, follistatin, proliferin, prostaglandin E1, prostaglandin E2, cytokine, tumor necrosis factor, erythropoietin, granulocyte colony-stimulating factor, granulocyte macrophage colony-stimulating factor, angiogenin, and mixtures and isoforms thereof.

17. The method of claim 1 or 9, wherein the treatment agent is selected from the group consisting of sol gel particles, calcium phosphate glass, iron, fibrin, gelatin, low molecular weight hyaluronic acid, chitin, bacterial polysaccharides, metals, and mixtures thereof.

18. The method of claim 1 or 9, further comprising delivering one or more of pacing or defibrillation voltages through the first lead to the first electrode.

* * * * *